(12) United States Patent  
Kankan et al.

(10) Patent No.: US 7,705,163 B2
(45) Date of Patent: Apr. 27, 2010

(54) PROCESS FOR THE PREPARATION OF CARVEDILOL

(75) Inventors: Rajendra Narayanrao Kankan, Maharashtra (IN); Dharmaraj Ramachandra Rao, Maharashtra (IN)

(73) Assignee: Cipla Limited, Mumbai (IN)

( * ) Notice: Subject to any disclaimer, the term of this patent is extended or adjusted under 35 U.S.C. 154(b) by 427 days.

(21) Appl. No.: 11/568,785

(22) PCT Filed: May 19, 2005

(86) PCT No.: PCT/GB2005/001978

§ 371 (c)(1),
(2), (4) Date: Jan. 11, 2007

(87) PCT Pub. No.: WO2005/113502

PCT Pub. Date: Dec. 1, 2005

(65) Prior Publication Data

US 2008/0234492 A1    Sep. 25, 2008

(30) Foreign Application Priority Data

May 20, 2004    (GB) ................................. 0411273.6

(51) Int. Cl.
C07D 209/82    (2006.01)
(52) U.S. Cl. ........................ 548/444; 548/416; 548/427; 548/439; 548/440
(58) Field of Classification Search .................. 548/444
See application file for complete search history.

(56) References Cited

U.S. PATENT DOCUMENTS

| 4,273,711 | A | * | 6/1981 | Lauer et al. .................. 548/440 |
| 4,503,067 | A | | 3/1985 | Wiedemann et al. |
| 4,697,022 | A | * | 9/1987 | Leinert ....................... 548/444 |
| 6,777,559 | B2 | | 8/2004 | Scalone et al. |
| 7,482,471 | B2 | * | 1/2009 | Chhabada et al. ........... 548/440 |
| 2003/0225289 | A1 | | 12/2003 | Matsubara et al. |

FOREIGN PATENT DOCUMENTS

| EP | 0 918 055 A1 | 5/1999 |
| EP | 0918055 A1 * | 5/1999 |
| WO | WO 2004/041783 A1 * | 5/2004 |
| WO | WO 2004/113296 A1 | 12/2004 |

OTHER PUBLICATIONS

Dörwald, F. Zaragoza. Side Reactions in Organic Synthesis: A Guide to Successful Synthesis Design, Weinheim: Wiley-VCH Verlag GmbH & Co. KGaA, 2005, Preface.*

Augstein, J. et al., "Some Cardiovascular Effects of a Series of Aryloxyalkylamines," Journal of Medicinal Chemistry, vol. 8, May 1965, Chemical Research Department, Pfizer Limited, Sandwich, Kent, Great Britain, pp. 356-367.
Foreign communication from a counterpart application—International Search Report, Aug. 22, 2005, 4 pages.
Foreign communication from a related counterpart application—International Preliminary Report on Patentability, PCT/GB2005/001978, Nov. 21, 2006, 7 pages.

* cited by examiner

*Primary Examiner*—Kamal A Saeed
*Assistant Examiner*—Valerie Rodriguez-Garcia
(74) *Attorney, Agent, or Firm*—Conley Rose, P.C.; Rodney B. Carroll

(57) ABSTRACT

A process for the preparation of carvedilol of formula (I) (I) either in enantiomeric substantially pure form, or as an enantiomeric mixture, optionally as a pharmaceutically acceptable salt thereof, which process comprises reacting 2,3-eopxypropoxy carbazole of formula (II) (II) or the R or S enantiomer thereof, with N-[2-(2-methoxy-phenoxy)ethyl]-benzylamine of formula (V) (V) to yield benzyl carvedilol of formula (VI) (VI) which is debenzylated by catalytic hydrogenation to yield carvedilol of formula (I), either in enantiomeric substantially pure form, or as an enantiomeric mixture, and if desired reacting the thus formed carvedilol of formula (I) with an inorganic or organic acid to yield a pharmaceutically acceptable salt thereof, and/or, if desired, separating the enantiomers. The above process is characterised in that reaction of said 2,3-epoxypropoxy carbazole of formula (II) with said N-[2-(2-methoxy-phenoxy)ethyl]-benzylamine of formula (V) is carried out in water as the reaction medium. The present invention further provides carvedilol of formula (I) prepared by a process as described above, and pharmaceutical compositions containing the same and therapeutic uses thereof.

18 Claims, No Drawings

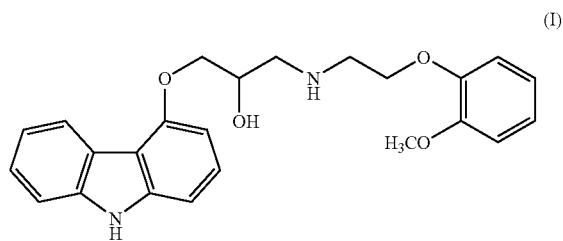

(I)

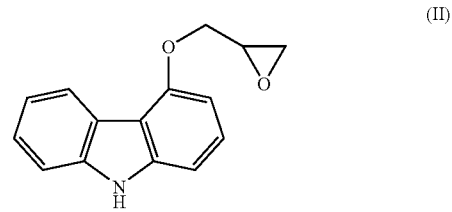

(II)

PROCESS FOR THE PREPARATION OF CARVEDILOL

The present invention is concerned with a new process for preparing 1-(9H-carbazol-4-yloxy)-3-[[2-(2-methoxyphenoxy)ethyl]amino]-2-propanol of formula (I)

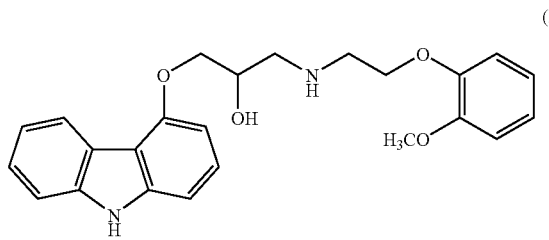
(I)

The above compound of formula (I) is known under the INN name of carvedilol and is used as a drug having antihypertensive, beta-adrenergic blocking and vasodilating activity.

The preparation of carvedilol has been known from DE 2815926, while the preparation of the R and S enantiomers has been described in DE 3313027. More particularly, 2,3-epoxypropoxy carbazole of formula (II)

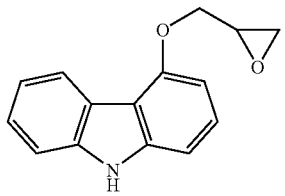
(II)

or the R or S enantiomer thereof, is reacted with 2-[2'-(methoxy)-phenoxy]-ethylamine of formula (III)

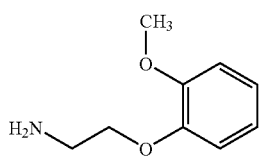
(III)

to produce carvedilol in a yield of 39 to 42%. A drawback of this known process is that in addition to the formation of carvedilol, the following bis compound of formula (IV) is also formed

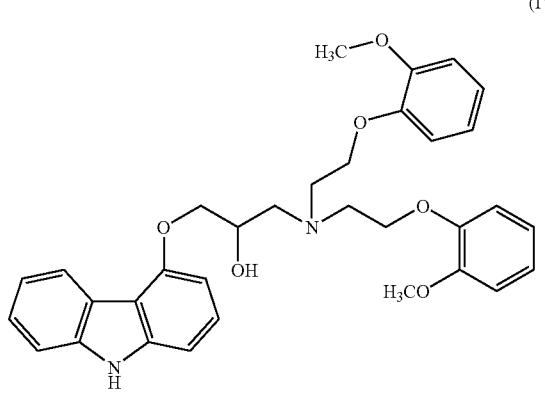
(IV)

Further processes for the preparation of carvedilol have also been described in DE 2815926. In Example 5 of DE 2815926, 2,3-epoxypropoxy carbazole of above formula (II) is reacted with the secondary amine N-[2-(2-methoxy-phenoxy)ethyl]-benzylamine of formula (V)

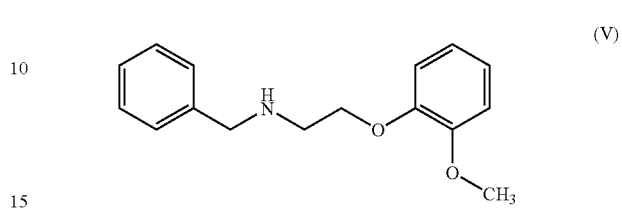
(V)

to yield benzyl carvedilol of formula (VI)

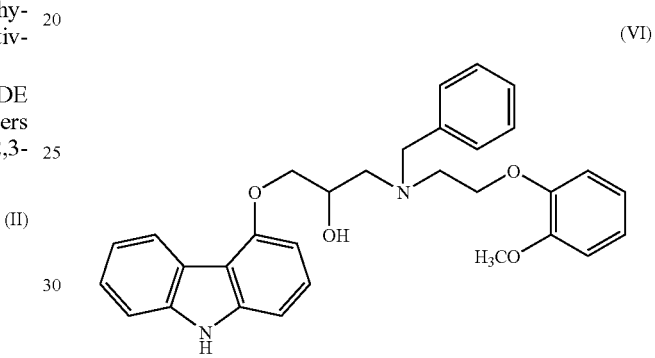
(VI)

The thus formed benzyl carvedilol of formula (VI) required column chromatography for separation.

EP 0918055 describes a process for the preparation of carvedilol, which is characterised in that 2,3-epoxypropoxy carbazole of formula (II) is reacted with N-[2-(2-methoxy-phenoxy)ethyl]-benzylamine of formula (V) in the presence of a protic organic solvent and the thus formed benzyl carvedilol of formula (VI) is debenzylated by catalytic hydrogenation.

The present invention now provides an improved process for the preparation of carvedilol of formula (I)

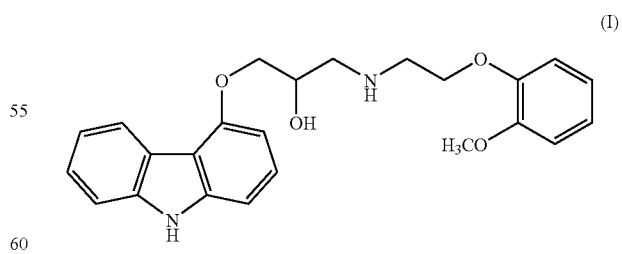
(I)

either in enantiomeric substantially pure form, or as an enantiomeric mixture, optionally as a pharmaceutically acceptable salt thereof, which process comprises reacting 2,3-epoxypropoxy carbazole of formula (II)

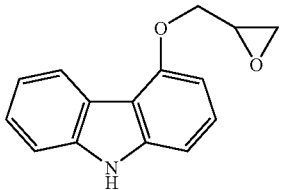

(II)

or the R or S enantiomer thereof, with N-[2-(2-methoxy-phenoxy)ethyl]-benzylamine of formula (V)

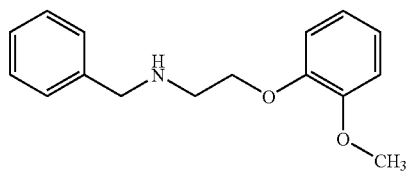

(V)

to yield the benzyl carvedilol of formula (VI)

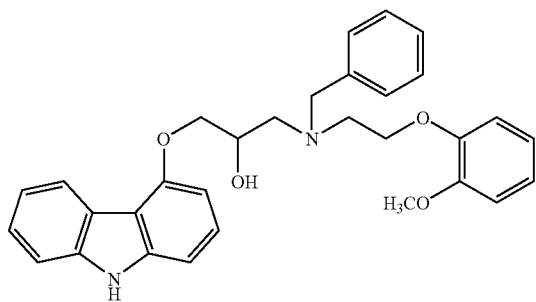

(VI)

which is debenzylated by catalytic hydrogenation to yield carvedilol of formula (I), either in enantiomeric substantially pure form, or as an enantiomeric mixture, and if desired reacting the thus formed carvedilol of formula (I) with an inorganic or organic acid to yield a pharmaceutically acceptable salt thereof, and/or, if desired, separating the enantiomers;

which process is characterised in that reaction of said 2,3-epoxypropoxy carbazole of formula (II) with said N-[2-(2-methoxy-phenoxy)ethyl]-benzylamine of formula (V) is carried out in water as the reaction medium.

Preferably in a process according to the present invention 2,3-epoxypropoxy carbazole of formula (II) is prepared from 4-hydroxy carbazole of formula (VII)

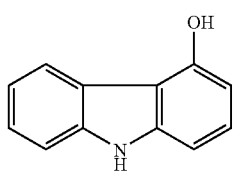

(VII)

which process step can also be characterised as being carried out in water as the reaction medium.

It is further preferred that in a process according to the present invention 4-hydroxy carbazole of formula (VII) is prepared from 1,2,3,9-tetrahydrocarbazole-4-one of formula (VIII)

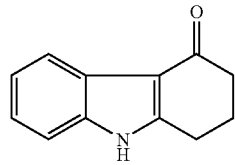

(VIII)

which process step can also be characterised as being carried out in water as the reaction medium.

A process according to the present invention of preparing carvedilol of formula (I), either in enantiomeric substantially pure form, or as an enantiomeric mixture, optionally as a pharmaceutically acceptable salt thereof, can thus be represented by the following reaction scheme

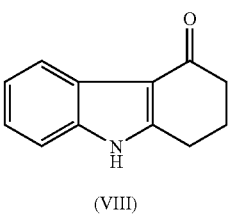

(VIII)

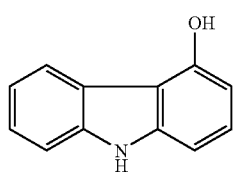

(VII)

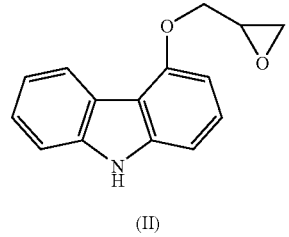

(II)

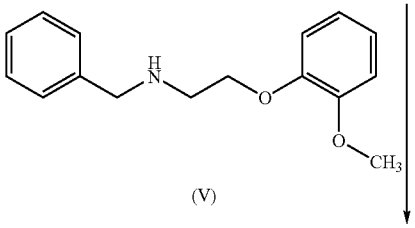

(V)

-continued

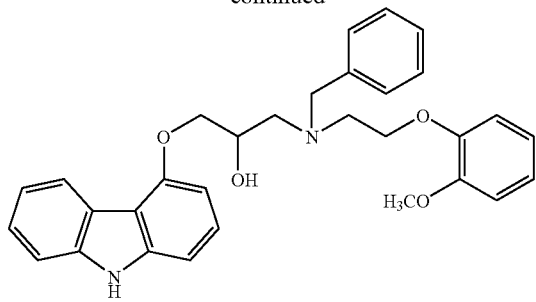

(VI)

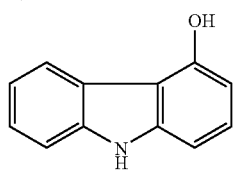

(I)

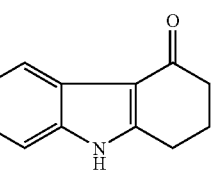

(VIII)

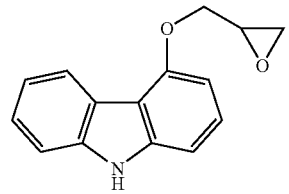

(VII)

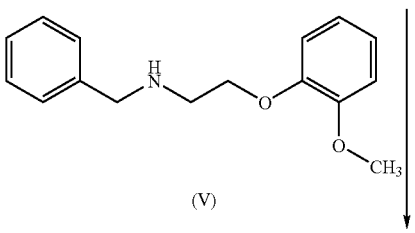

(II)

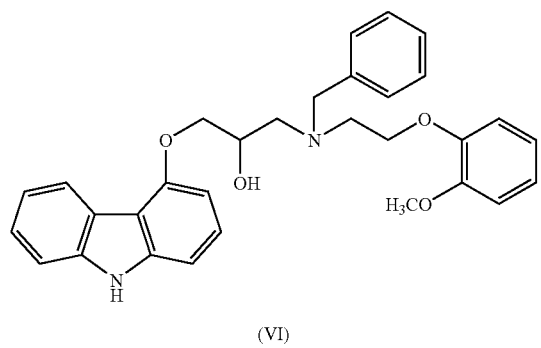

(V)

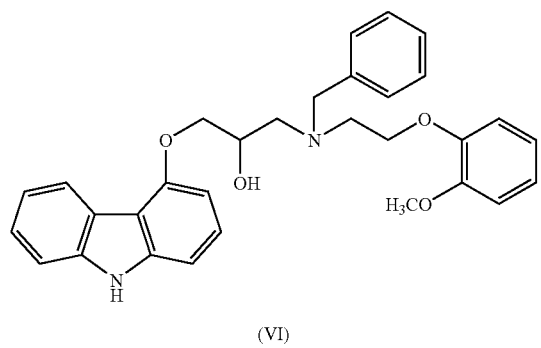

(VI)

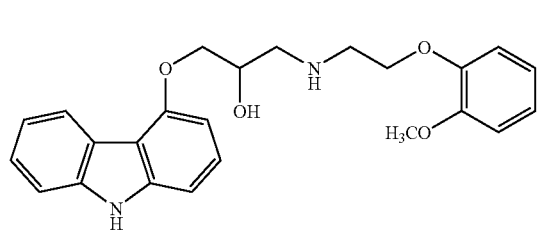

(I)

and if desired reacting the thus formed carvedilol of formula (I) with an inorganic or organic acid to yield a pharmaceutically acceptable salt thereof, and/or, if desired, separating the enantiomers, characterised in that at least for reaction of compounds of formulae (II) and (V), this process step is carried out in water as the reaction medium. More preferably, for a process as represented by the above reaction scheme each of the illustrated intermediate process steps leading to benzyl carvedilol of formula (VI) is carried out in water as the reaction medium.

A process according to the present invention is advantageous in that it allows the preparation of carvedilol of formula (I) from 1,2,3,9-tetrahydrocarbazole-4-one of formula (VIII) by intermediate process steps which up to and including the preparation of benzyl carvedilol of formula (VI) can each be carried out in water as the reaction medium. 1,2,3,9-tetrahydrocarbazole-4-one of formula (VIII) is a known compound and can be prepared under aqueous conditions from 1,3-cyclohexanedione and phenyl hydrazine, typically as described in Example 1 of U.S. Pat. No. 4,273,711. Intermediates (VII), (II) and (VI) can be isolated at each intermediate process stage; alternatively a process as represented by the above scheme can be carried out as a one-pot process. A process according to the present invention can thus offer the advantages of being environmentally friendly (with no organic solvent being used for the reaction), can achieve an improved yield compared to prior art processes and is industrially applicable for large scale production.

There is further provided by the present invention, therefore, a process of preparing carvedilol of formula (I), either in enantiomeric substantially pure form, or as an enantiomeric mixture, optionally as a pharmaceutically acceptable salt thereof, which can be represented by the following reaction scheme and if desired reacting the thus formed carvedilol of formula (I) with an inorganic or organic acid to yield a pharmaceutically acceptable salt thereof, and/or, if desired, separating the enantiomers, characterised in that the process steps leading to the preparation of benzyl carvedilol of formula (VI) are carried out as a one-pot process in water as the reaction medium.

Debenzylation of benzyl carvedilol of formula (VI) by catalytic hydrogenation can be carried out in a manner known per se in connection with the removal of a benzyl group. Preferably as a catalyst palladium on carbon is used. Suitably, hydrogen gas is bubbled through the reaction mixture at room temperature and the temperature is then raised to 45-50° C. and the bubbling of hydrogen gas is continued for a further 8 hours. Typically, the reaction mass is filtered to remove the catalyst and the filtrate is subsequently concentrated to remove solvent. The resulting contents can then be chilled, filtered and washed to provide carvedilol of formula (I).

Reaction of compounds of formulae (II) and (V) to yield benzyl carvedilol of formula (VI) is carried out in water as the reaction medium substantially as hereinbefore described and preferably also in the presence of a base, such as an alkali metal carbonate, typically potassium carbonate or the like. The reaction mixture is suitably heated and stirred for several hours and the resulting contents can then be cooled, filtered and washed to provide benzyl carvedilol of formula (VI).

N-[2-(2-methoxy-phenoxy)ethyl]-benzylamine of formula (V) can be prepared by techniques known in the art, for example as described in J. Med. Chem., 8 [1965], 356 to 367.

2,3-Epoxypropoxy carbazole of formula (II) can be prepared from 4-hydroxy carbazole of formula (VII) by reaction of the latter with epichlorohydrin in water as the reaction medium substantially as hereinbefore described and preferably also in the presence of a phase transfer catalyst, such as tetrabutyl ammonium bromide or the like. Suitably a base is present in the reaction mixture, such as an alkali metal hydroxide, typically sodium hydroxide or the like.

4-Hydroxy carbazole of formula (VII) is in turn prepared from 1,2,3,9-tetrahydrocarbazole-4-one of formula (VIII) in a process according to the present invention, typically by employing a catalyst known to be suitable for the hydration of double bonds, such as Raney nickel, in water as the reaction medium and again suitably in the presence of a base, such as an alkali metal hydroxide, typically sodium hydroxide or the like.

In a preferred embodiment, the reaction of compound II with compound V is carried out in the absence of an organic acid.

In a preferred embodiment, the reaction of compound II with compound V is carried out in the absence of an aprotic solvent.

In a preferred embodiment, the reaction of compound II with compound V is carried out in the absence of ethers, esters, ketones, amides, nitrites, hydrocarbons, hydrobromides, halogenated hydrocarbons, and aromatic solvents.

In a preferred embodiment, the reaction of compound II with compound V is carried out in the absence of dioxane, tetrahydrofuran, dimethoxyethane, diisopropylether, methyltertbutylether, ethyl acetate and methylacetate.

In a preferred embodiment, wherein each of the illustrated intermediate process steps leading to benzyl carvedilol of formula (VI) is carried out in the absence of an organic acid.

In a preferred embodiment, wherein each of the illustrated intermediate process steps leading to benzyl carvedilol of formula (VI) is carried out in the absence of an aprotic solvent.

In a preferred embodiment, wherein each of the illustrated intermediate process steps leading to benzyl carvedilol of formula (VI) is carried out in the absence of ethers, esters, ketones, amides, nitrites, hydrocarbons, hydrobromides, halogenated hydrocarbons, and aromatic solvents.

In a preferred embodiment, wherein each of the illustrated intermediate process steps leading to benzyl carvedilol of formula (VI) is carried out in the absence of dioxane, tetrahydrofuran, dimethoxyethane, diisopropylether, methyltertbutylether, ethyl acetate and methylacetate.

In a preferred embodiment, the reaction of compound II with compound V is carried out in the presence of water as the reaction medium in an amount such that the molar ratio of compound II to water is 1 to >=1.

In a preferred embodiment, the reaction of compound II with compound V is carried out in the presence of water as the reaction medium in an amount such that the molar ratio of compound II to water is 1 to >=10.

In a preferred embodiment, the reaction of compound II with compound V is carried out in the presence of water as the reaction medium in an amount such that the molar ratio of compound II to water is 1 to >=20.

In a preferred embodiment, the reaction of compound II with compound V is carried out in the presence of water as the reaction medium in an amount such that the molar ratio of compound II to water is 1 to >=40.

Typically, the reaction of compound II with compound V is carried out in the presence of water as the reaction medium in an amount such that the molar ratio of compound II to water is 1 to =<100.

In a preferred embodiment, the reaction of compound II with compound V is carried out in the presence of water as the reaction medium in an amount such that the weight ratio of compound II to water is 1 to >=0.5.

In a preferred embodiment, the reaction of compound II with compound V is carried out in the presence of water as the reaction medium in an amount such that the weight ratio of compound II to water is 1 to >=1.0.

In a preferred embodiment, the reaction of compound II with compound V is carried out in the presence of water as the reaction medium in an amount such that the weight ratio of compound II to water is 1 to >=2.0.

In a preferred embodiment, the reaction of compound II with compound V is carried out in the presence of water as the reaction medium in an amount such that the weight ratio of compound II to water is 1 to >=4.0.

Typically, the reaction of compound II with compound V is carried out in the presence of water as the reaction medium in an amount such that the molar ratio of compound II to water is 1 to =<10.

There is further provided by the present invention carvedilol of formula (I), either in enantiomeric substantially pure form, or as an enantiomeric mixture, optionally as a pharmaceutically acceptable salt thereof, prepared by a process substantially as hereinbefore described.

There is further provided by the present invention carvedilol of formula (I) as prepared by a process according to the present invention, for use in therapy.

Carvedilol of formula (I) as provided by a process according to the present invention is known to have vasodilatory and beta-adrenergic blocking action. Carvedilol of formula (I) as provided by the present invention is, therefore, suitable for the treatment and prophylaxis of circulatory and cardiac diseases, for example hypertension and angina pectoris.

The present invention further provide, therefore, a pharmaceutical composition for the treatment and prophylaxis of hypertension and/or angina pectoris, which composition comprises a pharmaceutically acceptable carrier and in a therapeutically effective amount carvedilol of formula (I) as provided by the present invention.

For the preparation of a pharmaceutical composition according to the present invention, carvedilol of formula (I) as provided by the present invention can be mixed in the usual manner with appropriate pharmaceutical carrier materials, aroma, flavoring and coloring materials as required and, for example, formulated into tablets, or with the addition of appropriate adjuvants, suspended or dissolved in water or in an oil.

Carvedilol of formula (I) as provided by the present invention can be administered enterally or parenterally in liquid or solid form. As injection medium, it is preferable to use water which contains the additives usual in the case of injection solutions, such as stabilizing agents, solubilizing agents and/or buffers. Additives of this type include, for example, tartrate and citrate buffers, ethanol, complex-forming agents (such as ethylenediaminetetraacetic acid and the non-toxic salts thereof) and high molecular weight polymers (such as liquid polyethylene oxide) for viscosity regulation. Solid carrier materials are, for example starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavoring and/or sweetening materials.

There is further provided by the present invention carvedilol of formula (I) as provided by the present invention, for use in the manufacture of a medicament for the treatment of hypertension and/or angina pectoris.

There is still further provided by the present invention a method of treating a subject suffering from or susceptible to hypertension and/or angina pectoris, which method comprises administering to such subject a therapeutically effective amount of carvedilol of formula (I) as provided by the present invention.

In actual administration of carvedilol of formula (I) as provided by the present invention, e.g., in the treatment of hypertension or angina pectoris, the appropriate dosage is of course dependent on the condition of the patient and the specific infirmity to be treated. In general, treatment should begin with small doses (e.g. 100 mg) and be increased gradually depending upon the patient's response. The dosage can be increased at 5 to 7 day intervals until an average daily dosage of 100 to 300 mg is reached. For maintenance, 2 to 4 doses a day are usually required. These dosage levels will generally be appropriate, both for achieving a vasodilating effect, i.e., for reducing blood pressure, and for inhibition of adrenergic beta-receptor activity.

The present invention will now be further illustrated by the following Example, which does not limit the scope of the invention in anyway.

EXAMPLE

Step 1: Preparation of 4-Hydroxy Carbazole

To a reactor containing water (1 L) was added Raney nickel (35 g) followed by 1,2,3,9-tetrahydrocarbazole-4-one (50 g) and sodium hydroxide (15 g). The contents were heated to reflux and maintained for about 20 hours. The catalyst was filtered off and the filtrate was acidified to obtain a solid, which was filtered and dried to obtain the title compound.

When necessary, the title compound was further purified by dissolving in 10% sodium hydroxide solution, treating with activated charcoal and precipitation from dilute hydrochloric acid to give off-white to grey crystals of 4-hydroxy carbazole in 50% yield.

Step 2: Preparation of 2,3-Epoxypropoxy Carbazole

4-Hydroxy carbazole (60 g) obtained in step 1 was charged into a reactor containing water (90 ml). Epichlorohydrin (64.2 g) and tetrabutyl ammonium bromide (6.3 g) were then charged into the reactor under stirring. 50% Sodium hydroxide solution (78 g) was added slowly in 2-3 hours into the reaction mass at about 30° C. After completion of reaction, ethyl acetate (315 ml) and potable water (315 ml) were charged into the reaction mass. The lower aqueous layer was separated and discarded. The ethyl acetate layer was washed with potable water to obtain neutral pH and dried over anhydrous sodium sulphate. The ethyl acetate is distilled out under vacuum below 55° C. to about 100 ml. The reaction mass was chilled to 0-5° C. and filtered and dried at 50-60° C. to give the title compound (50 g) (64%).

Step 3: Preparation of N-Benzyl Carvedilol

Epoxy carbazole (10 g) obtained in step 2 was charged to water (500 ml) under stirring followed by potassium carbonate (112 g) and N-[2-(2-methoxy-phenoxy)ethyl]-benzylamine (140 g) at room temperature. The contents were heated to 80-90° C. and stirred for 3 hours at 85-90° C. The reaction mass was cooled to 30-35° C. and water was decanted. Fresh water (1 L) was added and the mass stirred to obtain a solid which was filtered and washed with water to obtain the title compound (205 g) (99%).

Step 4: Preparation of Carvedilol

Benzyl carvedilol (205 g) obtained in step 3 was charged to ethyl acetate (2400 ml) and water (240 ml). The contents were stirred and 10% palladium on carbon (20 g) was added at room temperature. Hydrogen gas was bubbled at room temperature. The temperature was raised to 45-50° C. and bubbling was continued for 8 hours. The reaction mass was filtered to remove the catalyst and the filtrate was concentrated to remove solvent (about 2 L). The contents were chilled to 15-20° C., filtered and washed with chilled ethyl acetate (50 ml) to give carvedilol (140 g) (84%).

The invention claimed is:

1. A process for the preparation of carvedilol of formula (I):

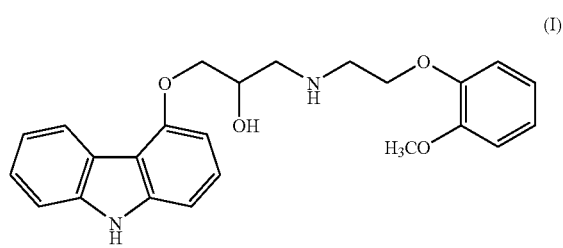

either in enantiomerically pure form, or as an enantiomeric mixture, optionally as a pharmaceutically acceptable salt thereof, which process comprises reacting 2,3-epoxypropoxy carbazole of formula (II):

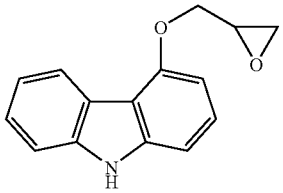
(II)

in the form of the R or S enantiomer, or a mixture thereof, with N-[2-(2-methoxyphenoxy)ethyl]-benzylamine of formula (V):

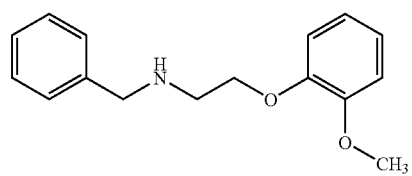
(V)

to yield benzyl carvedilol of formula (VI):

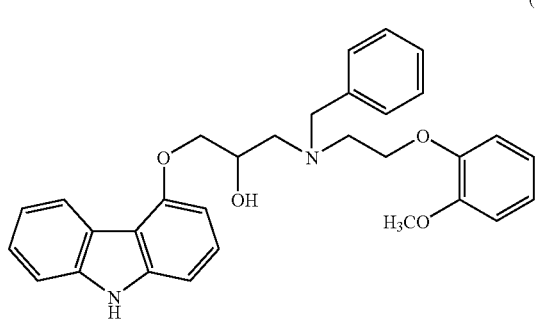
(VI)

which is debenzylated by catalytic hydrogenation to yield carvedilol of formula (I), either in enantiomerically pure form, or as an enantiomeric mixture, and if desired reacting the thus formed carvedilol of formula (I) with an inorganic or organic acid to yield a pharmaceutically acceptable salt thereof, and/or, if desired, separating the enantiomers;

which process is characterized in that reaction of said 2,3-epoxypropoxy carbazole of formula (II) with said N-[2-(2-methoxy-phenoxy)ethyl]-benzylamine of formula (V) is carried out in water as the reaction medium and in the absence of an organic solvent.

2. The process according to claim 1, wherein 2,3-epoxypropoxy carbazole of formula (II) is prepared from 4-hydroxy carbazole of formula (VII):

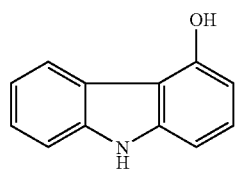
(VII)

which preparation of 2,3-epoxypropoxy carbazole of formula (II) is characterized as being carried out in water as the reaction medium.

3. The process according to claim 2, wherein said 4-hydroxy carbazole of formula (VII) is prepared from 1,2,3,9-tetrahydrocarbazole-4-one of formula (VIII):

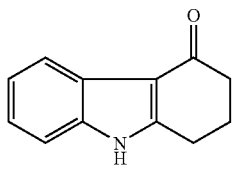
(VIII)

which process step is characterized as being carried out in water as the reaction medium.

4. A process of preparing carvedilol of formula (I), either in enantiomerically pure form, or as an enantiomeric mixture, optionally as a pharmaceutically acceptable salt thereof, represented by the following reaction scheme:

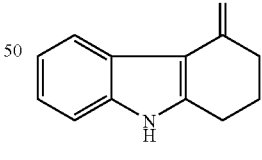
(VIII)

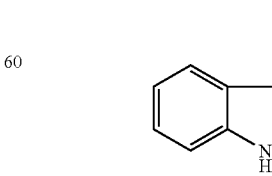
(VII)

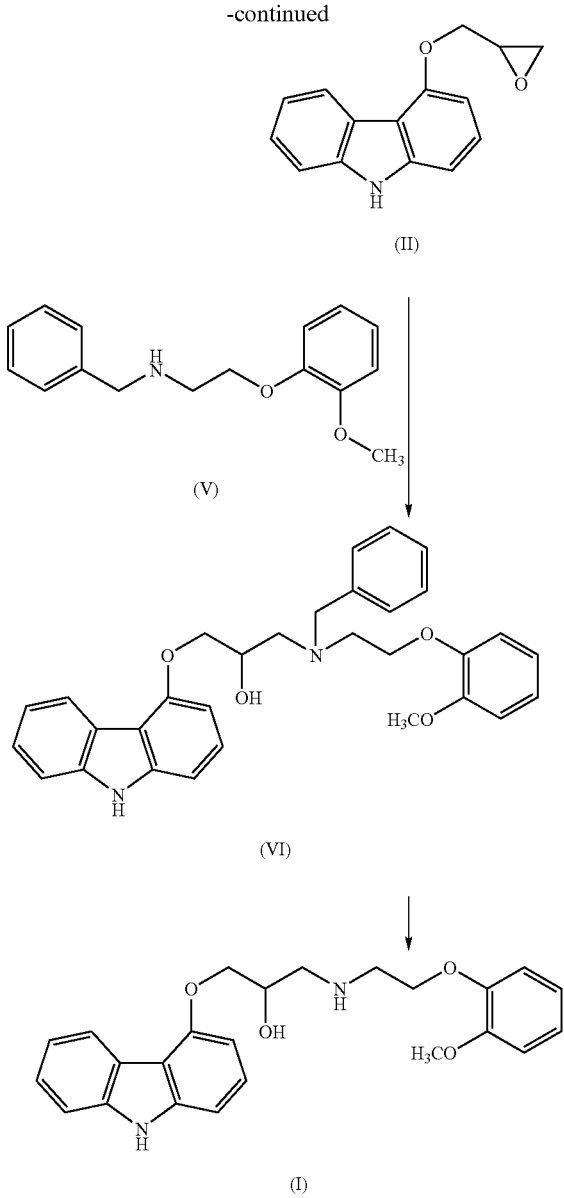

and if desired reacting the thus formed carvedilol of formula (I) with an inorganic or organic acid to yield a pharmaceutically acceptable salt thereof, and/or, if desired, separating the enantiomers, which process is characterized in that at least for reaction of compounds of formulae (II) and (V), this process step is carried out in water as the reaction medium and the reaction of compounds of formulae (II) and (V) is carried out in the absence of an organic solvent.

5. The process according to claim 4, wherein each of the process steps leading to benzyl carvedilol of formula (VI) is carried out in water as the reaction medium.

6. The process according to claim 1, wherein debenzylation of benzyl carvedilol of formula (VI) is carried out in the presence of palladium on carbon as a catalyst.

7. The process according to claim 1, wherein reaction of compounds of formulae (II) and (V) to yield benzyl carvedilol of formula (VI) is carried out in the presence of a base.

8. The process according to claim 7, wherein said base is potassium carbonate.

9. The process according to claim 2, wherein 2,3-epoxypropoxy carbazole of formula (II) is prepared from 4-hydroxy carbazole of formula (VII) by reaction of the latter with epichlorohydrin in water as the reaction medium.

10. The process according to claim 9, wherein 4-hydroxy carbazole of formula (VII) is reacted with epichlorohydrin in the presence of a phase transfer catalyst.

11. The process according to claim 10, wherein said phase transfer catalyst is tetrabutyl ammonium bromide.

12. The process according to claim 9, which is carried out in the presence of a base.

13. The process according to claim 12, wherein said base is sodium hydroxide.

14. The process according to claim 3, wherein 4-hydroxy carbazole of formula (VII) is prepared from 1,2,3,9-tetrahydrocarbazole-4-one of formula (VIII) using Raney nickel as catalyst.

15. The process according to claim 14, which is carried out in the presence of a base.

16. The process according to claim 15, wherein said base is sodium hydroxide.

17. The process according to claim 4, wherein each of the process steps leading to benzyl carvedilol of formula (VI) is carried out in the absence of an aprotic solvent.

18. The process according to claim 1, wherein the reaction of compound II with compound V is carried out in the presence of water as the reaction medium in an amount such that the molar or weight ratio of compound II to water is 1 to >=1.

* * * * *

UNITED STATES PATENT AND TRADEMARK OFFICE
CERTIFICATE OF CORRECTION

PATENT NO. : 7,705,163 B2
APPLICATION NO. : 11/568785
DATED : April 27, 2010
INVENTOR(S) : Rajendra Narayanrao Kankan et al.

It is certified that error appears in the above-identified patent and that said Letters Patent is hereby corrected as shown below:

On the title page, Item (57) Abstract, correct the following:

Lines 1-2, Replace "preparation of carvedilol of formula (I) (I) either" with -- preparation of carvedilol of formula (I) either --

Lines 4-5, Replace "2,3-eopxypropoxy carbazole of formula (II) (II) or the R" with -- 2,3-epoxypropoxy carbazole of formula (II) or the R --

Line 7, Replace "of formula (V) (V) to yield" with -- of formula (V) to yield --

Line 8, Replace "formula (VI) (VI) which is" with -- formula (VI) which is --

Signed and Sealed this

Fifteenth Day of June, 2010

David J. Kappos
*Director of the United States Patent and Trademark Office*